(12) United States Patent
Sajiki et al.

(10) Patent No.: US 10,912,486 B2
(45) Date of Patent: Feb. 9, 2021

(54) MEDICAL POSTURE RETAINER

(71) Applicant: ENGINEERING SYSTEM CO., LTD., Nagano (JP)

(72) Inventors: Osamu Sajiki, Matsumoto (JP); Yoshiki Kawamura, Matsumoto (JP)

(73) Assignee: ENGINEERING SYSTEM CO., LTD., Nagano (JP)

( * ) Notice: Subject to any disclaimer, the term of this patent is extended or adjusted under 35 U.S.C. 154(b) by 84 days.

(21) Appl. No.: 15/763,816

(22) PCT Filed: Oct. 7, 2016

(86) PCT No.: PCT/JP2016/079954
§ 371 (c)(1),
(2) Date: Mar. 27, 2018

(87) PCT Pub. No.: WO2017/073301
PCT Pub. Date: May 4, 2017

(65) Prior Publication Data
US 2018/0279906 A1    Oct. 4, 2018

(30) Foreign Application Priority Data
Oct. 29, 2015  (JP) .................. 2015-212908

(51) Int. Cl.
*A61B 5/055*  (2006.01)
*A61B 6/04*  (2006.01)
(Continued)

(52) U.S. Cl.
CPC .............. *A61B 5/0555* (2013.01); *A61B 5/70* (2013.01); *A61B 6/04* (2013.01); *A61F 5/3707* (2013.01);
(Continued)

(58) Field of Classification Search
None
See application file for complete search history.

(56) References Cited

U.S. PATENT DOCUMENTS

| | | | | |
|---|---|---|---|---|
| 3,337,883 A | * | 8/1967 | Duncan | A47G 9/1009 5/638 |
| 3,762,404 A | * | 10/1973 | Sakita | A43B 17/035 602/6 |

(Continued)

FOREIGN PATENT DOCUMENTS

| | | |
|---|---|---|
| JP | 8-215172 | 8/1996 |
| JP | 11-113687 | 4/1999 |

(Continued)

OTHER PUBLICATIONS

Sistanley Jones Lima Bispo, Aug. 2015, Materials Research vol. 18 pp. 4 (Year: 2015).*

*Primary Examiner* — David R Hare
*Assistant Examiner* — Adam C Ortiz
(74) *Attorney, Agent, or Firm* — Smith, Gambrell & Russell, LLP.

(57) ABSTRACT

The present invention is a medical posture retainer having a mat and a core member. The mat includes an airtight bag and a cushion layer. The airtight bag is a cover of the mat and has a gas barrier property. An exhaust valve for deflation is attached to the bag. The cushion layer is formed of particles in the bag. The core member includes a plate-like support that is attached to a side face of the hag to keep a certain rise height, and a stopper that is attached to the upper face and the lower face of the airtight bag to restrict the rise height. The core member is attached before deflation of the bag so as to impart a shape necessary for receiving a specific part of a human body.

1 Claim, 6 Drawing Sheets

(51) Int. Cl.
*A61G 13/12* (2006.01)
*A61B 5/00* (2006.01)
*A61F 5/37* (2006.01)

(52) U.S. Cl.
CPC ......... *A61G 13/121* (2013.01); *A61G 13/126* (2013.01); *A61G 13/1275* (2013.01)

(56) References Cited

U.S. PATENT DOCUMENTS

| | | | |
|---|---|---|---|
| 5,971,006 A | | 10/1999 | Seigerschmidt |
| 6,131,219 A | * | 10/2000 | Roberts ................ A47G 9/1027 5/636 |
| 9,205,014 B1 | * | 12/2015 | Nesley ................ A61G 13/121 |
| 2003/0135927 A1 | * | 7/2003 | Hsia .................... A47G 9/1009 5/640 |
| 2012/0255126 A1 | * | 10/2012 | Abdo .................. A47G 9/1009 5/638 |

FOREIGN PATENT DOCUMENTS

| | | |
|---|---|---|
| JP | 2003-052492 | 2/2003 |
| JP | 2005-066141 | 3/2005 |
| JP | 3115580 | 9/2005 |
| JP | 2007-029249 | 2/2007 |
| JP | 2008-264010 | 11/2008 |
| JP | 2009-112380 | 5/2009 |
| JP | 2010-119415 | 6/2010 |
| JP | 2013-244197 | 12/2013 |
| JP | 2014-45890 | 3/2014 |
| JP | 3192339 | 7/2014 |
| WO | 00/41599 | 7/2000 |

* cited by examiner (a) (b) (c)

MEDICAL POSTURE RETAINER

TECHNICAL FIELD

The present invention relates to a medical posture retainer that retains a posture of a subject or a patient stably during medical practices such as diagnostic procedures using MRI or the like, radiation therapies, and various surgical operations. In this Specification, "posture" is used as a term indicating a specific position or pose of a human body.

BACKGROUND ART

For instance, during a diagnostic procedure using MRI or a radiation therapy, it is necessary to ensure that a specific body part of a human, namely, a subject or a patient is stable and do not move and that the posture of the human body is retained.

Mats that are conventionally known and used for supporting or packaging articles contain predetermined amounts of particles together with air in an airtight bag provided with an exhaust valve for deflation.

When an article is placed on the upper face of the airtight bag of this type of mat, the bag may be partly dented due to the weight of the article. If the air in the bag is exhausted in this state, the filling density of the particles may be increased and the bag is set to fit a part of the article, whereby the article can be supported stably on the bag.

This type of mat is used not only for supporting or packaging articles but as a cushion to support a human body. Furthermore, it gains attention also in the medical field. It is expected to be used as a medical appliance for posture retention during a procedure for an image diagnosis, a surgical operation or the like (see Patent Documents 1, 2).

This type of mat may be used for retaining a posture of a human body during a procedure for a diagnosis or a surgical operation. The mat, which may also be used for holding a specific part of a human body not to move for a certain period of time, is called a posture retaining mat (hereinafter, this may be called a mat simply for the purpose of convenience).

When the posture retaining mat is used in a procedure of MRI imaging of the head, the procedure is conducted while the subject is lying on his/her back on a bed. It is necessary to ensure that the head can escape being applied with any excessive force and that the head and neck are stable and do not move.

When the subject lies on his/her back on the bed, the subject may have his/her proper posture by lifting his/her head slightly. For retaining this posture, there would be a difference in height between the surface of the bed and the head supported above the bed.

The posture retaining mat is used to decrease the difference in height between the bed and the head so as to stabilize the posture. However, the particles in the airtight bag of the conventional posture retaining mat are smooth and slippery beads of a synthetic resin. Therefore, even if a suitable amount of the particles P are piled to a predetermined height, the piled particles may slide down to result in a gentle slope, and thus, a sufficient rise height cannot be kept.

When the posture retaining mat is used as a pillow, a head H may be placed thereon, an airtight bag 16 of a mat 15 may be deflated using an air pump (not shown), and thus, the mat 15 may be set with a space d remaining between the mat 15 and parts of the human body, namely, the head H and the neck N. Although the head H is supported at the small area of the occiput by the mat plane of the posture retaining mat 15 as shown in FIG. 11(a), the both sides of the head H and the both sides of the neck N cannot be supported by the mat plane as shown in FIGS. 11(b) and 11(c).

In FIG. 11(a), the space between the mat 15 and the parts of human body, namely, the head H and the neck N, is indicated with a dashed line d.

When the airtight bag is deflated in a state where parts of the posture retaining mat 15 are pressed against the neck N and the head H as shown in FIG. 13(a), the mat can be set in a close contact with the both sides of the head H and the both sides of the neck N as shown in FIGS. 13(b) and 13(c). However, a part of the bottom and the both side edges of the posture retaining mat 15 may be lifted, rendering the support by the posture retaining mat 15 unstable on the bed B. As a result, the head H cannot be stabilized at a fixed position.

PRIOR ART DOCUMENTS

Patent Documents

Patent Document 1: JP-A-2007-29249
Patent Document 2: JP-A-2009-112380

SUMMARY OF THE INVENTION

Problems to be Solved by the Invention

Particles of the synthetic resin are usually so smooth and slippery, and thus, despite the effort to pile a suitable amount of the particles to a certain height, the piled particles may slide down and result in a gentle slope. As a result, a sufficient rise height cannot be kept. When the airtight bag is deflated in a state where a part of the posture retaining mat is pressed against a human body, the posture retaining mat can be set in a close contact with the human body. However, the posture retaining mat itself may be placed unstably on the bed, and thus, the posture cannot be kept stably.

The problem is not limited to retention of head. Similar problems can occur when the posture retaining mat is used to hold firmly a subject/patient on the bed with the limbs bent at certain angles or to hold firmly the subject/patient at the waist on the bed.

Means for Solving the Problems

The present invention enables to stably retain a human body with a combination of a mat and a core member. The mat has an airtight bag filled with strata of particles. The core member is most characterized in that it supports at least one part of the airtight bag filled with the particles, thereby imparting the mat surface with a shape required to receive a specific part of a human body. In the present specification, the expression "impart with a shape" is used to mean "shape" or "form".

Effects of the Invention

In the present invention, an airtight bag filled with particles is supported at least partly by a core member so as to support a specific part of a human body with a bulge or a dent as a shape imparted to the surface of the airtight bag of the mat. The airtight bag is then deflated to set the mat, such that the mat is fixed in a close contact with the human body so as to fit the specific part of the human body. As a result, the posture of the subject or the patient can be stabilized during a procedure for a diagnosis or a therapy.

BRIEF DESCRIPTION OF THE DRAWINGS

FIGS. 3(a)-3(c): FIG. 3(a) is a view showing a plate-like support attached to be used as a core member in Example 1, FIG. 3(b) is a view showing another example of plate-like support, and FIG. 3(c) is a view showing a stopper attached to be used as the core member in Example 1;

FIGS. 6(a) and 6(b): FIG. 6(a) is a view showing an example that uses straight supporting rods as core members to prevent or control airtight bag shrinkage caused by deflation, and FIG. 6(b) is a magnified cross-sectional view taken along the line A-A of FIG. 6(a);

FIG. 11(a)-11(c): FIG. 11(a) is a cross-sectional view showing a conventional posture retaining mat, the mat receives a head and a neck on dents formed on the upper face of the mat and an airtight bag is deflated to set the mat, FIG. 11(b) is a cross-sectional view taken along the line C-C of FIG. 11(a), and FIG. 11(c) is a cross-sectional view taken along the line D-D of FIG. 11(a);

FIGS. 13(a) to 13(c): FIG. 13(a) is a cross-sectional view showing a conventional posture retaining mat pressed against a head and a neck of a human body for receiving the head and the neck in dents formed on the upper face of the mat, thereby deflating an airtight bag to set the mat, FIG. 13(b) is a cross-sectional view taken along the line E-E of FIG. 13(a), and FIG. 13(c) is a cross-sectional view taken along the line F-F of FIG. 13(a).

MODE FOR CARRYING OUT THE INVENTION

Figure 1:
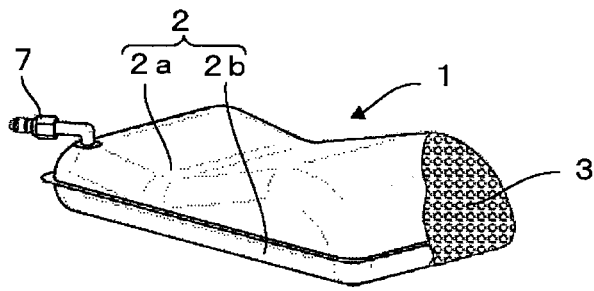
FIG. 1 is a partially broken perspective view showing a mat of Example 1, imparted with a shape required to receive a specific part of a human body on the surface of the mat.

The medical posture retainer according to the present invention comprises a combination of a mat and a core member. The mat comprises an airtight bag and a cushion layer. The airtight bag is a cover of the mat for supporting a human body and retaining the posture. The airtight bag has a gas barrier property, and an exhaust valve for deflation is attached to the airtight bag. The cushion layer comprises strata of particles filled in the airtight bag. The core member to be combined with the mat is imparted with a shape required to support at least a part of the airtight bag filled with the particles so as to restrict the rise height and to receive a specific part of a human body on the mat surface.

Hereinafter, the respective components constituting the medical posture retainer of the present invention are explained.

(1) Airtight Bag Used as a Cover of a Mat

It is required that a fabric used for the airtight bag as a cover of a mat is airtight and further desirably soft for not causing discomfort to a human body.

A fabric satisfying the above conditions can be obtained by, for instance, coating or laminating a resin on a film-like fabric to impart a gas barrier property to the fabric. Since the fabric is required to be durable, it is preferably made of nylon. For the film to be coated or laminated on the fabric, PV (vinyl chloride) and PU (polyurethane) are preferred since they may be fused and adhered easily to the fabric.

Thickness of fabric may impose a great influence on softness. Thickness may preferably be decreased to enhance softness. However, when strength and a gas barrier property required for a cover of a mat are taken into consideration, the thickness is preferably in a range from about 1 mm to about 0.2 mm. For CT examination or MRI examination, an X-ray transmission type nonmagnetic material may be selected preferably.

(2) Cushion Layer

The cushion layer comprises strata of particles filled in the airtight bag.

Though there is no particular limitation on the size, shape, and hardness of the particles, preferably the particle diameter is decreased as much as possible to fit exactly the shape of a specific part of a human body. Further, light-weight materials are desired from the viewpoint of handling or operations to fit the shape of a specific part of the human body. Therefore, for this purpose, particles of a foamed synthetic resin is suitable, and particles of foamed PS (polystyrene) and foamed PE (polyethylene) are particularly preferred.

When giving priority to shape preservation to fit a specific part of a human body, a foamed PS resin with a low expansion ratio may be preferred; when giving priority to cushioning property, a foamed PU resin or a foamed PE resin with a high expansion ratio may be used. These resins can be blended with each other to impart intermediate characteristics. The airtight bag as a cover of the mat may comprise a rectangular upper face member and a rectangular lower face member filled therebetween with a predetermined amount of particles in advance to form a cushion layer and sealed airtight at their peripheries. Further, an exhaust valve for deflation is attached at a part of the upper face member.

3) Core Member

The core member is imparted with a shape required for supporting at least a part of the airtight bag filled with the particles, so that the mat can receive a specific part of a human body.

Figure 7:
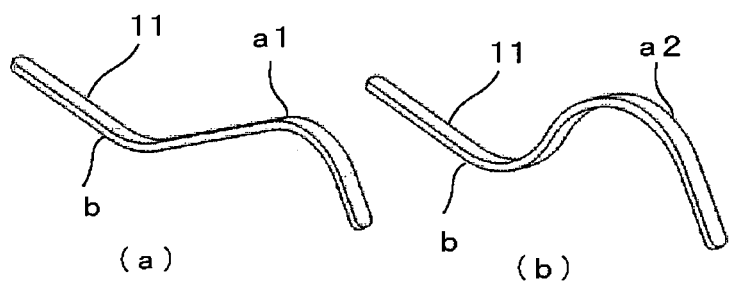
FIG. 7 includes FIGS. 7(a) and 7(b), both of which showing examples where supporting rods are used as the core members of Example 2, each of the supporting rods is bent along the longitudinal direction to have a predetermined upward curve and a predetermined downward curve.

As mentioned below, the core member is used in various forms such as "plate-like support 4" (see FIG. 3(a)) oriented to keep the rise height of the mat, "stopper 6" (see FIG. 3(b)) to restrict the rise height of the mat, "supporting rod 11" (see FIG. 7) to support the mat in a longitudinal direction so as to deform it forcibly, and "plate-like holder 12" (see FIG. 9) that holds and presses a specific part of a human body with a mat.

EXAMPLES

Hereinafter, Examples of the present invention will be described, referring to a specific posture of a subject undergoing an MRI for instance. In these Examples, the subject retains a certain posture with his/her head and neck supported on the mat.

Example 1

Figure 2:
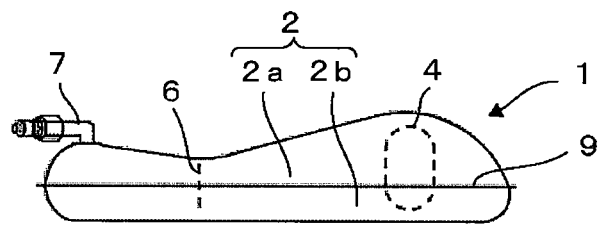
FIG. 2 is side view of the mat of Example 1.

In this Example shown in FIGS. 1 and 2, an airtight bag 2 serving as a cover of a mat 1 is prepared. The airtight bag 2 comprises a rectangular upper face member 2a and a rectangular lower face member 2b filled therebetween in advance with a predetermined amount of particles P to form a cushion layer 3. Rectangular face members 21 and 2b define longitudinal (length) and width directions of bag 2. At the same time, a plate-like support 4 selected as a first core member and a stopper 6 selected as a second core member are attached to the upper face Member 2a and the lower face member 2b, and then, the upper face member 2a and the lower face member 2b are joined and sealed together at their peripheries. An exhaust valve 7 for deflation is attached at a corner of the upper face member 2a.

The plate-like support 4 used as the first core member is a self-supportable and flexible plate as shown in FIG. 3(a), and it is sewn to the (inner or outer) side face of the airtight bag 2. Plate-like support 4 is oriented substantially perpendicular to the longitudinal and width directions of upper and lower face members 21, 2b in bridging over the joint 9 between the upper face member 2a and the lower face member 2b, thereby keeping adhesiveness and airtightness, so that the plate-like support 4 serves to keep a certain width and a certain rise height of the airtight bag 2.

Since the plate-like support 4 as the first core member is attached to the (inner or outer) side face of the airtight bag 2 to bridge over the joint 9 between the upper face member 2a and the lower face member 2b, the airtight bag 2 can keep its rise height corresponding to the height of the plate-like support 4 used as the first core member 1, at least for the entire width of the plate-like support 4.

The plate-like support is not limited to a simple plate. In an alternative embodiment as shown in FIG. 3(b), a pair of upward arms 5a, 5a and a pair of downward arms 5b, 5b are provided to the both side edges of the plate-like support 5, while bands 8 are attached to the upper face member 2a and the lower face member 2b. The plate-like support 5 is inserted to be interposed between the upper face member 2a and one of the band 8 and further between the lower face member 2b and the other band 8, and at the same time, the upward arms 5a and the downward arms 5b are hooked in the respective bands 8, 8, so that the plate-like support 5 can be attached in a removable manner to the outer face or the inner face of the airtight bag 2.

Figure 3:
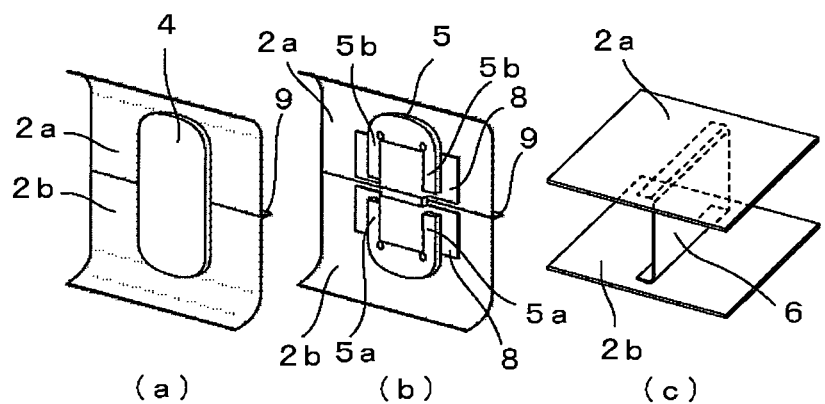
FIG. 3 includes

The second core member comprises the stopper 6. As shown in FIG. 3 (c), the stopper 6 is a soft sheet of a predetermined length. It connects the upper face and the lower face of the airtight bag 2, namely, the fabric of the upper face member 2a and the fabric of the lower face member 2b, thereby restricting the rise height of the airtight bag 2 not to exceed the predetermined height.

Figure 4:
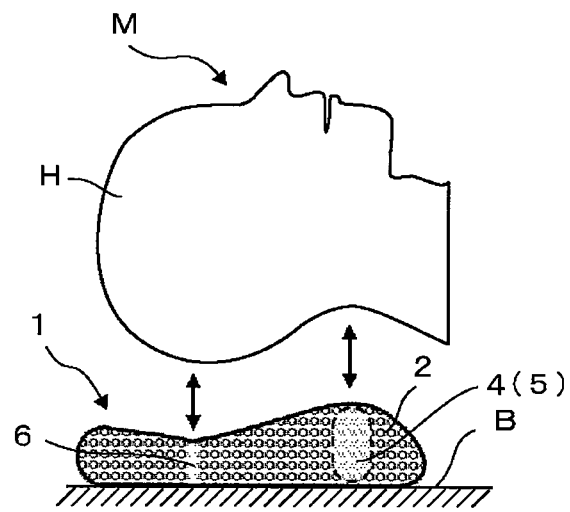
FIG. 4 is a view showing how to place the head of a subject on the mat of Example 1.

As shown in FIG. 4, the upper face and the lower face of the airtight bag 2 are connected with the stopper 6 at a part supporting the head H of the subject M, thereby restricting the rise height of the airtight bag 2. Meanwhile, the plate-like support 4 (or 5) is attached to the airtight bag 2 at a part supporting the neck N. This plate-like support is attached bridging over the joint 9 between the upper face member 2a and the lower face member 2b, thereby keeping a rise height higher than the average height of the airtight bag 2. In this manner, the surface of the mat 1 is imparted in advance with a curved shape including a dent necessary for receiving the head H of human body and a bulge to support the neck N.

When the subject M lies on his/her back, the subject can take a comfortable posture with the head H being supported by the neck N that extends from the shoulders in the upward tilting direction. In a diagnostic procedure using imaging, the subject M is held stably on the plane of the mat 1 to keep the posture.

The surface of the mat 1 is provided in advance with a curved shape necessary for receiving the head H and the neck N of the subject M. The shape does not necessarily fit precisely the shapes of the head H and the neck N of the subject M as long as the curved surface is provided to roughly fit a head H and a neck N.

Figure 5:
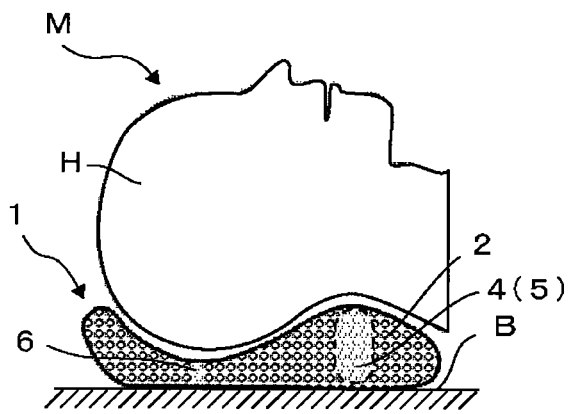
FIG. 5 is a view showing the mat of Example 1, on which the head of the subject is placed and the airtight bag is deflated.

In FIG. 5, the subject M lies on his/her back on the bed B. At the position for a pillow, the mat 1 shaped to have curves for receiving the head H and the neck N is placed. The head H of the subject M is received by the dent for receiving head, the neck N is supported by the bulge so that the shape of the mat 1 is adapted to the shape of the head H and the neck N of the subject as much as possible. Then, an air pump (not shown) is inserted into the exhaust valve 7 to deflate the airtight bag 2.

With reduction of the pressure inside the airtight bag 2, the filling density of the particles P in the airtight bag 2 is increased. Due to the reduction of volume of the airtight bag 2, the cushion layer 3 is deformed to adapt to the shape of the head H of the subject M. The neck N is supported at the bulge having the rise height determined by the height of the support 4 (or 5), and the head H is received and held stably in the dent formed by the stopper 6.

The subject M is held stably at the head H and the neck N so that the subject M is prevented from moving any parts of the body, which may ensure that the posture of the subject M (including the head H and the neck N) is held stably during the procedure of imaging the head H such as CT, MRI and PET.

The aforementioned operations are not limited to the stable retention of the posture of human body in a case of image diagnosis using CT, MRI, PET or the like. The same points can be applied to hold stably of a human body at the head to a bed for a radiation therapy or a surgical therapy. Further, the object to be held stably is not limited to a human head. Limbs or any other human body parts bent at a certain angle can be held and retained stably on the bed. Further, it can be employed to hold stably the entire human body.

Example 1 refers to an example for using together the plate-like support 4 (or 5) as the first core member and the stopper 6 as the second core member. It is also possible to use each of these plate-like support 4 (or 5) and the stopper 6 independently. This point can be applied to diagnostic procedures using imaging such as CT, MRI, PET, a radiation therapy and any other surgical therapies in Examples below.

Example 2

Figure 6:
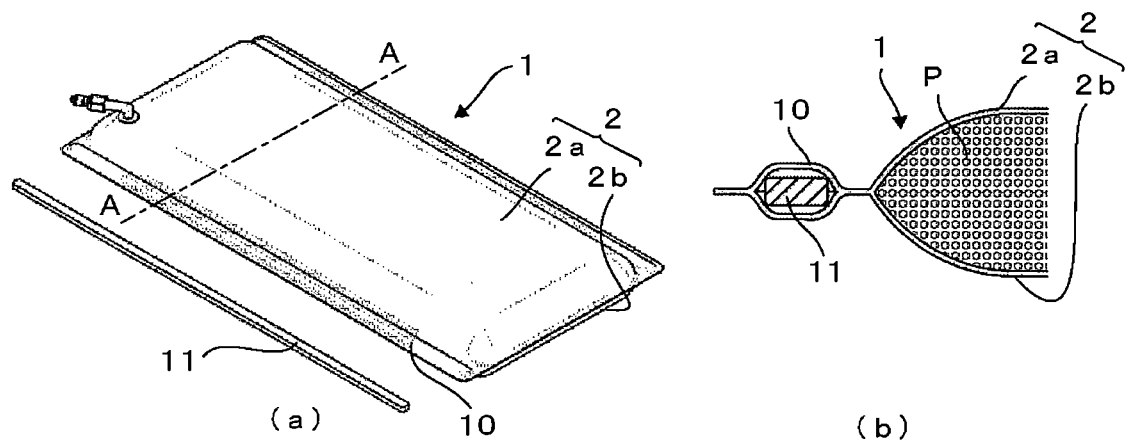
FIG. 6 includes
Figure 8:
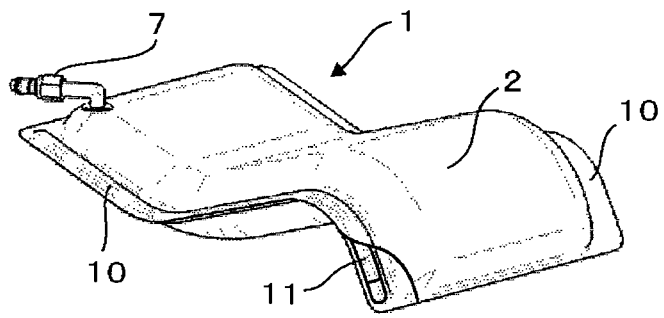
FIG. 8 is a partially broken perspective view showing an example of deforming a mat by using the bent supporting rods as the core members of Example 2.

In Example 2, supporting rods 11 are used for the core members. FIG. 6(a) shows that the upper face member 2a and the lower face member 2b of the airtight bag 2 as a cover of the mat 1 are joined and sealed at their peripheries, and sheaths 10 are formed at the long side edges. As shown in FIG. 6(b), a straight supporting rod 11 is inserted from an opening at one end of each of the sheaths 10 to prevent shrinkage, which may be caused by the deflation, in the longitudinal direction of the airtight bag 2. Each of the supporting rods 11 is bent to have an upward curve a1 and a downward curve b in the longitudinal direction as shown in FIG. 7(a), and the bent supporting rods 11 are inserted into the respective sheaths 10 on the both side edges of the airtight bag 2. In this case, the airtight bag 2 is bent and deformed in accordance with the shape of the bent supporting rods 11. When the bent and deformed airtight bag 2 is deflated, the airtight bag 2 may be set in the deformed state, and as shown in FIG. 8, the airtight bag 2 is imparted with a curved shape including a bulge and a dent adapted to the shapes of the upward curve a1 and the downward curve b of the supporting rods 11.

The bulge of the airtight bag 2, which is formed by inserting the bent supporting rods 11, imparts a plane to support the neck of the subject as shown in FIG. 5, while the dent of the same airtight bag imparts a plane to receive the head of the subject. The airtight bag 2 serves not only to receive the neck and the head of the subject, but if necessary, the airtight bag can be bent and deformed to have an upward curve a2 with a greater rise height as shown in FIG. 7(b), so that it can further be bent to have a shape necessary to receive any parts of human body other than the head.

In this Example, the supporting rods 11 are inserted in a removable manner into the sheaths 10 formed at the long side edges of the airtight bag 2. However, the positions for forming the sheaths 10 are not limited to the long side edges of the airtight bag 2. The position can be determined suitably to the central area in the longitudinal direction of the airtight bag 2 or to the short side edge(s) of the airtight bag 2 for instance, and the supporting rods 11 bent and deformed to have a predetermined shape are used to impart the airtight bag 2 with a shape suitable for receiving a specific part of the human body. Further, the process for attaching the supporting rods 11 to the airtight bag 2 is not limited to the example of inserting the supporting rods 11 into the sheaths 10. The supporting rods 11 can be integrated with or attached in a removable manner to the airtight bag 2 by any means such as bonding, sewing or the like.

Example 3

Figure 9:
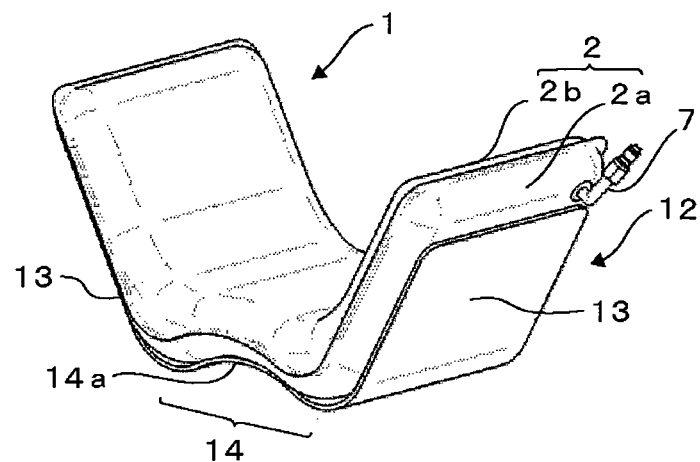
FIG. 9 is a perspective view showing a mat supported by an elastic plate-like holder as the core member of Example 3.
Figure 10:
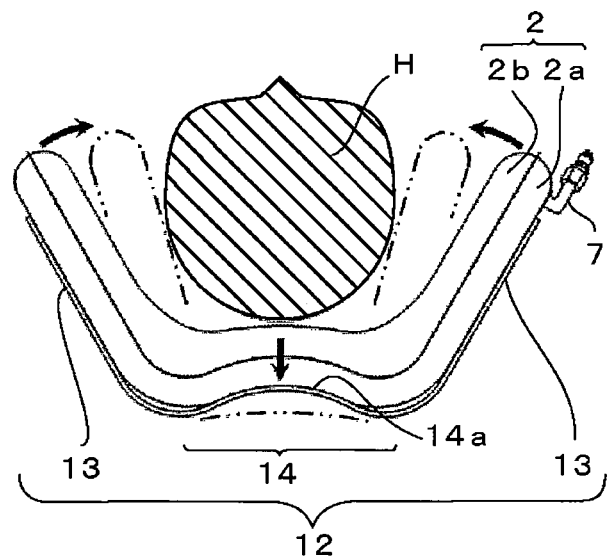
FIG. 10 is a view showing the mat of Example 3, the distance between a pair of supporting flat portions of the plate-like holder used as the core member of Example 3 is decreased due to the weight of the head of the subject, whereby the mat supported by the supporting flat portions is pressed against the both sides of the head.
Figure 11:
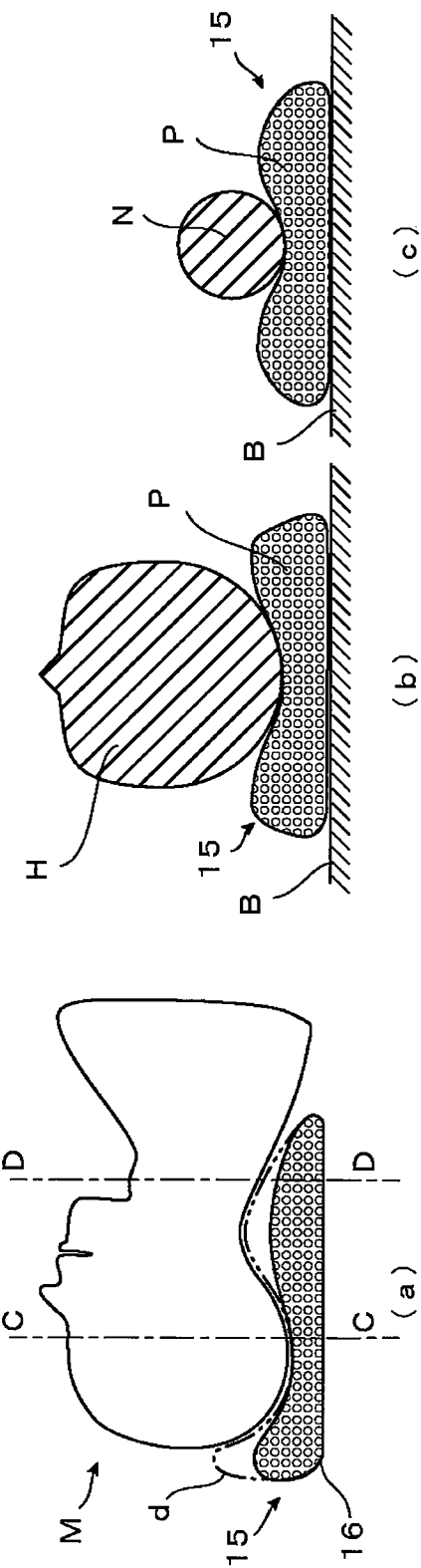
FIG. 11 includes
Figure 12:
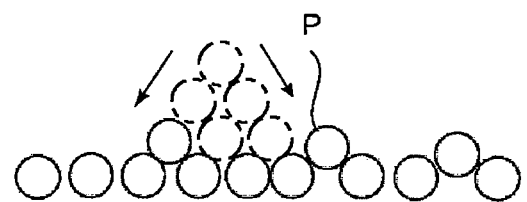
FIG. 12 is a view showing that piled smooth particles in a mat slide down and result in a gentle slope so as to make it impossible to keep a sufficient rise height.
Figure 13:
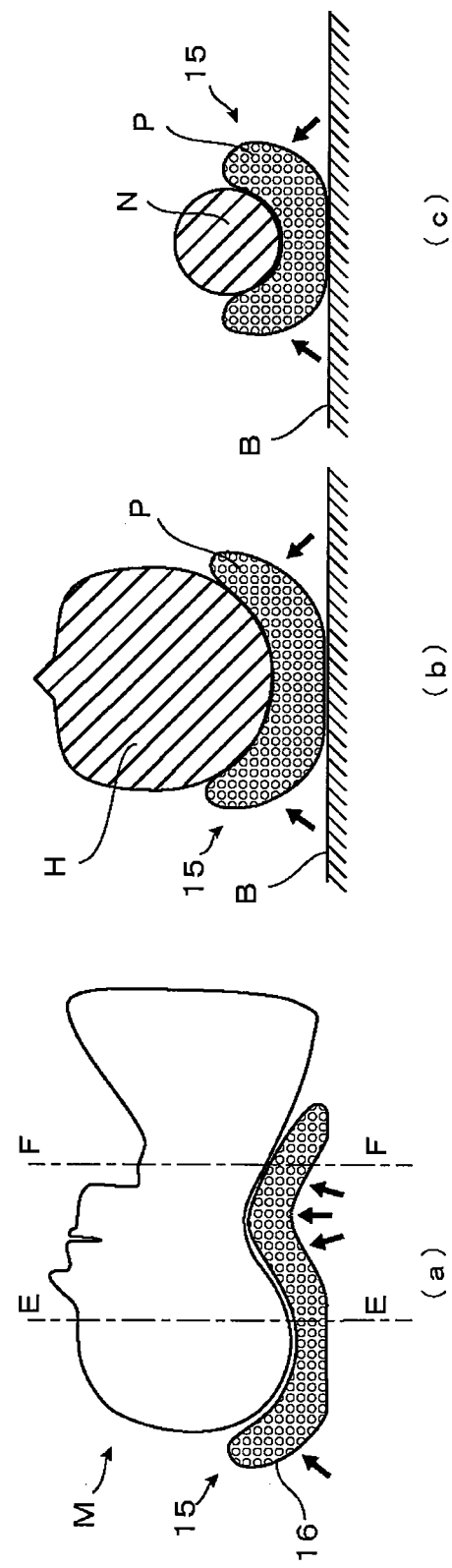
FIG. 13 includes

The core member used in Example 3 is an elastic plate-like holder 12 formed in advance to have a predetermined "W" shape as shown in FIG. 9. The plate-like holder 12 is composed of a pair of supporting flat portions 13, 13 and a hinge portion 14 that connects and supports the supporting flat portions 13, 13 so that the supporting flat portions 13, 13 may open outward in their upwardly inclined posture. At the central area of the hinge portion 14, a convex ridge 14a is formed. A concave region on either side of ridge 14a connects the convex ridge to flat portions 13, 13 to give holder 12 its "W" shape. In this Example, the hinge portion 14 supports the airtight bag 2 of the mat 1 placed bridging over the supporting flat portions 13, 13 of the holder 12. When the head H is placed on the central area of the hinge portion 14 as shown in FIG. 10, the convex ridge 14a formed in the middle of the hinge portion 14 is pressed downwardly the weight of the head H whereby the supporting flat portions 13, 13 that are opened outwardly get closer to each other.

In this manner, the airtight bag 2 supported to bridge over the supporting flat portions 13, 13 may be pressed against the both sides of the head H. When this airtight bag 2 is deflated in this state, the airtight bag 2 is set in the state being in a close contact with the both sides of the head H, retaining the head H at a fixed position. The airtight bag 2 serves to retain not only the head H, but any other parts of human body such as arms and legs. When supporting any other specific parts, the supporting flat portions 13, 13 of the holder 12 as the core member are elastically deformed due to the weight applied by the specific part of the human body, so as to press the airtight bag 2, so that the specific part of the human body can be retained at a fixed position.

In any of the Examples, a check valve is usually used for the exhaust valve. The check valve for deflation has an air supply-exhaust hole whose deflation side being in the forward direction and whose aspiration side being in the reverse direction. At the time of using the medical posture retainer, an air pump is attached to automatically open the valve of the air supply-exhaust hole. By driving the air pump, the airtight bag 2 is deflated to reduce the volume, thereby setting the cushion layer. After the use, the air supply-exhaust valve is opened manually, so that air is sucked into the airtight bag to recover the initial volume of the airtight bag. The air supply-exhaust hole may not always have the check valve, but it may be a simple ventilation hole opened at a part of the airtight bag.

Even a simple ventilation hole formed at a part of the airtight bag may serve for exhaustion. Namely, when the airtight bag is applied with pressure in use due to the weight of the human body, the air in the airtight bag may be exhausted through the ventilation hole, whereby the volume of the airtight bag is reduced and the filling density of the cushion layer is increased so that the cushion layer can be set. On the other hand, when the pressure applied to the airtight bag is released after the use, resilience of the cushion layer and repulsion of the core member act on the airtight bag, so that the airtight bag that has reduced its volume sucks air from the ventilation hole so as to recover its initial volume. Due to this reason, the air supply-exhaust hole formed at the airtight bag is not limited to an air supply-exhaust hole having a check valve. Even a simple ventilation hole formed at a part of the airtight bag can work to reduce the volume of the airtight bag by deflation, and recover the initial volume by sucking air. For instance, in a case of holding for a short-time in a simple X-ray shooting that ends with a momentary shooting, a ventilation hole formed at a part of the airtight bag may be sufficient.

As mentioned above, according to the present invention, various types of core members can be used to be combined with the airtight bag. The core member may be included inside the airtight bag, or it may support the airtight bag from the outside, thereby retaining the mat and forcibly deforming the mat to be adapted to the shape of the core member. As a result, the mat can have a surface imparted with a shape including a bulge and a dent necessary for receiving specific parts of a human body.

INDUSTRIAL APPLICABILITY

The present invention can be applied widely to any cases where body movement of a subject or a patient is required to be prevented or controlled to keep a certain posture, during medical practices including diagnostic procedures using imaging such as CT, MRI and PET, radiation therapies and any other surgical operations.

EXPLANATIONS OF LETTERS OR NUMERALS 1 mat
2 airtight bag
2a upper face member
2b lower face member
3 cushion layer
4,5 plate-like supports
5a,5b arms 6 stopper
7 exhaust valve
8 band
9 joint
10 sheath
11 supporting rod
12 holder
13 supporting flat portion
14 hinge portion
14a ridge
P particles
M subject
H head
N neck

The invention claimed is:

1. A medical posture retainer comprising a mat and a core member, wherein
the mat comprises an airtight bag extending in longitudinal and width directions and a cushion layer,
the airtight bag, as a cover of the mat supporting a human body and retaining a posture of the human body, has a gas barrier property and is formed with an air supply-exhaust hole for deflating the airtight bag at the time of use of the medical posture retainer for volume reduction of the airtight bag and for allowing the volume-reduced airtight bag to suck air after the use,
the cushion layer comprises strata of particles to fill the airtight bag and to be set by deflation of the airtight bag,
the core member comprises a support plate and a stopper, the support plate being oriented substantially perpendicularly with respect to both the longitudinal and width directions of the airtight bag and being attached to either an inner side face or an outer side face of the airtight bag, the support plate having rigidity so as to keep a predetermined rise height of the airtight bag at a part supporting a neck of the human body, the stopper being attached to an upper face and a lower face of the airtight bag for restricting the rise height of the mat at a part supporting a head of the human body,
the airtight bag has a rectangular upper face member joined to a rectangular lower face member at a joint, and
the support plate bridges over the joint between the face members.

* * * * *